US008470862B2

(12) United States Patent
Heino et al.

(10) Patent No.: US 8,470,862 B2
(45) Date of Patent: Jun. 25, 2013

(54) TREATMENT OR PREVENTION OF HYPOTENSION AND SHOCK

(75) Inventors: Riitta Heino, Turku (FI); Tiina Leino, Piikkiö (FI); Tarja Lehtimäki, Sauvo (FI)

(73) Assignee: Recro Pharma, Inc., Malvern, PA (US)

( * ) Notice: Subject to any disclaimer, the term of this patent is extended or adjusted under 35 U.S.C. 154(b) by 0 days.

(21) Appl. No.: 13/096,387

(22) Filed: Apr. 28, 2011

(65) Prior Publication Data
US 2011/0294862 A1    Dec. 1, 2011

Related U.S. Application Data

(63) Continuation of application No. 11/641,953, filed on Dec. 20, 2006, now abandoned, which is a continuation of application No. 10/111,628, filed as application No. PCT/FI00/00935 on Oct. 27, 2000, now abandoned.

(60) Provisional application No. 60/162,120, filed on Oct. 29, 1999.

(51) Int. Cl.
*A01N 43/50* (2006.01)
*A61K 31/415* (2006.01)

(52) U.S. Cl.
USPC ......................................... 514/385; 514/396

(58) Field of Classification Search
USPC ................................................ 514/396, 385
See application file for complete search history.

(56) References Cited

U.S. PATENT DOCUMENTS

| | | | |
|---|---|---|---|
| 4,910,214 A | 3/1990 | Karjalainen et al. | |
| 5,091,402 A | 2/1992 | Kalso et al. | |
| 5,485,827 A | 1/1996 | Zapol et al. | |
| 5,571,840 A | 11/1996 | Mayor et al. | |
| 5,713,907 A | 2/1998 | Hogendijik et al. | |
| 6,716,867 B1 | 4/2004 | Aantaa et al. | |
| 7,001,609 B1 | 2/2006 | Matson et al. | |
| 2003/0022926 A1 | 1/2003 | Lavand Homme | |
| 2003/0077227 A1 | 4/2003 | Dugger | |
| 2003/0124191 A1 | 7/2003 | Besse et al. | |
| 2005/0281752 A1 | 12/2005 | Duggar, III | |
| 2008/0021074 A1 | 1/2008 | Cartt | |
| 2008/0131483 A1 | 6/2008 | Abdulrazik | |

FOREIGN PATENT DOCUMENTS

| | | |
|---|---|---|
| GB | 2206880 | 1/1989 |
| WO | 9102505 | 3/1991 |
| WO | 9505820 | 3/1995 |
| WO | 97/12874 | 4/1997 |
| WO | 9949854 | 10/1999 |
| WO | 0265941 | 8/2002 |

OTHER PUBLICATIONS

Anttila, M. et al., "Bioavailability of dexmedetomidine after extravascular doses in healthy subjects", Br J Clin Pharmacol, 2003, 56:691-693.
Hall, J.E. et al., "Sedative, Amnestic, and Analgesic Properties of Small-Dose Dexmedetomidine Infusions", Anesth Analg., 2000, 90:699-705.
Office Action dated Apr. 26, 2012 received in U.S. Appl. No. 12/781,628.
Gomez-Vasquez et al., "Clinical analgesic efficacy and side effects of dexmedetomidine in the early postoperative period after arthroscopic knee surgery," Journal of Clinical Anesthesia (2007) 19(8):576-582.
Chrysostomou et al., "Dexmedetomidine: sedation, analgesia and beyond," Expert Opin Drug Metab Toxicol (2008) 4 (5):619-627.
Official Action dated Dec. 1, 2005 from U.S. Appl. No. 10/111,628, filed Aug. 23, 2002.
Kivisto, K.T. et al., "Pharmacokinetics and pharmacodynamics of transdermal dexmedetomidine", European Journal of Clinical Pharmacology, 1994, 46:345-349.
Karadas, B. et al., "Additive interaction of intraperitoneal dexmedetomidine and topical nimesulide, celecoxib, and DFU for antinocieception", Pharmacology, 2007, 556 (1-3):62-68.
Onttonen, T. et al., The Mechanical Antihyperalgesic Effect of Intrathecally Administered MPV-2426, a Novel.
Karaaslan, D. et al., "Comparison of Buccal and Intramuscular Dexmedetomidine Premedication for Arthroscopic Knee Surgery", J. Clin. Anesth., 2006, 18(8):589-593.
Cohen, M.S. et al., "Intranasal Dexmedetomidine for Sedation during CT Scanning", Amer. Society of Anesth., Annual Meeting Abstracts, Oct. 20, 2008, A998.
International Search Report dated Sep. 19, 2011 from International Patent Application No. PCT/US2011/020462, filed Jan. 7, 2011.
Angst et al., "Comparative analgesic and mental effects of increasing plasma concentrations of dexmedetomidine and alfentanil in humans," Anesthesiology (2004) 101(3):744-752.
Ugur et al., "Intrathecal infusion therapy with dexmedetomidine-supplemented morphine in cancer pain," Acta Anaesthesiol Scand (2007) 51(3):388.
Final Office Action dated Oct. 12, 2012 received in copending U.S. Appl. No. 12/781,628.
Kanazi et al., "Effect of low-dose dexmedetomidine or clonidine on the characteristics of bupivacaine spinal block," Acta Anaesthesiol Scand (2006) 50(2):222-227.
Ebert et al., "The effects of increasing plasma concentrations of dexmedetomidine in humans," Anesthesiology (2000) 93(2):382-394.
Eisenach et al., "Antinociceptive and Hemodynamic Effects of a Novel α2-Adrenergic Agonist, MPV-2426, in Sheep", Anesthesiology, 1999, 91:1425-1436.
Official Action dated Oct. 28, 2010 from U.S. Appl. No. 11/641,953, filed Dec. 20, 2006.
Official Action dated Jul. 26, 2010 from U.S. Appl. No. 11/641,953, filed Dec. 20, 2006.
Official Action dated dated Apr. 8, 2005 from U.S. Appl. No. 10/111,628, filed Aug. 23, 2002.
Official Action dated Aug. 25, 2004 from U.S. Appl. No. 10/111,628, filed Aug. 23, 2002.
International Search Report dated May 3, 2001 from International Patent Application No. PCT/FI00/00935, filed Oct. 27, 2000.

*Primary Examiner* — Yong Chong
(74) *Attorney, Agent, or Firm* — Pepper Hamilton LLP

(57) ABSTRACT

A method for the prevention and treatment of hypotension and shock due to low peripheral resistance, comprising administering to a mammal in need thereof an effective amount of a certain imidazole derivative or pharmaceutically acceptable ester or salt thereof, and a method for the treatment of cardiopulmonary resuscitation, comprising administering to a mammal in need thereof an effective amount of a certain imidazole derivative or pharmaceutically acceptable ester or salt thereof.

13 Claims, 2 Drawing Sheets

TREATMENT OR PREVENTION OF HYPOTENSION AND SHOCK

This is a continuation of application Ser. No. 11/641,953, filed Dec. 20, 2006 now abandoned, which is a continuation of application Ser. No. 10/111,628, with a §371 date of Aug. 23, 2002 now abandoned, which is a national stage application under §371 of International Application No. PCT/FI00/00935, filed Oct. 27, 2000, which claims the benefit of U.S. Provisional Application No. 60/162,120, filed Oct. 29, 1999, all of which are incorporated herein by reference.

BACKGROUND OF THE INVENTION

The present invention relates to a method for the prevention or treatment of hypotension and shock due to low peripheral resistance. Further, the present invention relates to a method for the treatment of cardiopulmonary resuscitation. Accordingly, the present invention relates to a method for the prevention or treatment of hypotension and shock due to low peripheral resistance by administering an imidazole derivative of the formula 1:

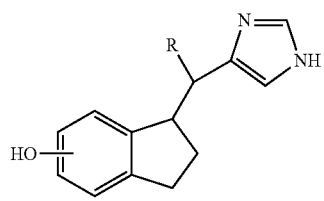

(I)

wherein R is hydrogen or methyl, or a pharmaceutically acceptable ester or salt thereof.

Further, the present invention relates to a method for the treatment of cardiopulmonary resuscitation by administering an imidazole derivative of formula 1 or a pharmaceutically acceptable ester or salt thereof.

The present invention also relates to the use of an imidazole derivative of formula 1, or a pharmaceutically acceptable ester or salt thereof, in the manufacture of a medicament for the prevention or treatment of hypotension and shock due to low peripheral resistance. Further, the present invention also relates to the use of an imidazole derivative of formula 1, or a pharmaceutically acceptable ester or salt thereof, in the manufacture of a medicament for the treatment of cardiopulmonary resuscitation.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The preparation of the imidazole derivatives of formula 1 in general has been described in WO 97/12874. Enteral, topical, and parenteral routes of administration and their use as $\alpha_2$-adrenoceptor agonists useful in the treatment of hypertension, glaucoma, migraine, diarrhea, ischemia, addiction to chemical substances, anxiety, especially preoperative anxiety, and different neurological, musculosketal, psychiatric and cognition disorders as well as a sedative and an analgesic agent, nasal decongestant, and as an adjunct to anaesthesia are discussed in WO 97/12874.

$\alpha_2$-Adrenoceptor agonists, such as dexmedetomidine, are known to induce a characteristic pattern of cardiovascular responses including e.g., bradycardia and hypotension and therefore they are typically considered as potential candidates for the treatment of hypertension.

DETAILED DESCRIPTION OF THE INVENTION

Applicants have surprisingly discovered that unlike other pure $\alpha_2$-adrenoceptor agonists, the imidazole derivatives of formula 1 do not decrease the blood pressure after intravenous, intramuscular or subcutaneous administration in a mammal. Accordingly, they cause an increase in the blood pressure with a reflectory decrease in heart rate after the administration. Thus, the imidazole derivatives of formula 1, or a pharmaceutically acceptable ester or salt thereof, can be used in situations where returning the blood from peripheral circulation to the central circulation is needed, like in circulatory shock due to low resistance of peripheral circulation and cardiac arrest. Further, the advantage of the compounds of the present invention compared to adrenalin which is commonly used in these situations, is the lack of direct stimulation of the heart i.e., the heart rate does not raise and cause further ischemia of the heart. Accordingly, an object of the invention is to provide a method for the prevention or treatment of hypotension and shock due to low peripheral resistance by administering an imidazole derivative of formula 1, or a pharmaceutically acceptable ester or salt thereof to a mammal. Further, an object of the invention is to provide a method for the treatment of cardiopulmonary resuscitation by administering an imidazole derivative of formula or a pharmaceutically acceptable ester or salt thereof to a mammal.

The preferred compound of the present invention is 3-(1 H-imidazol-4-ylmethyl)-indan-5-ol.

It should be noted that the method for the treatment of hypotension and shock due to low peripheral resistance encompasses all of the potential conditions that require the treatment of hypotension and shock, e.g., hypotension due to vasodilatation, anaphylactic shock, septic shock and post heart surgery shock.

The precise amount of the drug to be administered to a mammal for the prevention and treatment of hypotension and shock due to low peripheral resistance and for the treatment of cardiopulmonary resuscitation is dependent on numerous factors known to one skilled in the art, such as, the compound to be administered, the general condition of the patient, the condition to be treated, the desired duration of use, the type of mammal, the method of administration etc. The desired dose can be administered intravenously, using a bolus dose or by a steady infusion, intramuscularly or subcutaneously. For example, the dose of 3-(1H-imidazol-4-ylmethyl)-indan-5-ol administered intravenously to a human can be from about 10 to 500 µg/patient, preferably about 30-200 µg/patient.

One skilled in the art would recognize the dosage forms suitable in the method of the present invention. The injections or infusions may contain one or more diluents or carriers.

Figure 1:
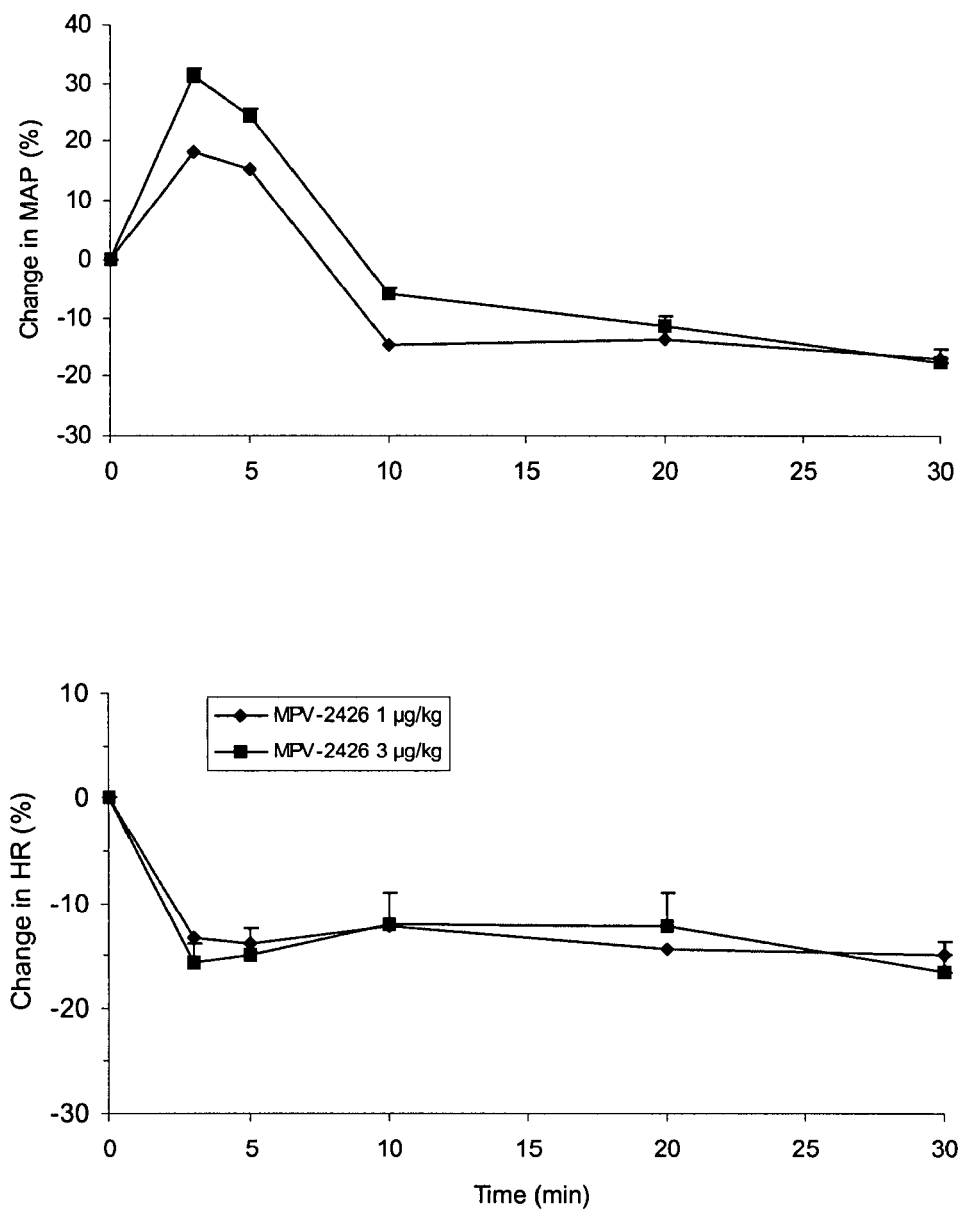
FIG. 1 shows the time-course of mean arterial pressure (MAP) (upper) and heart rate (HR) (lower) in anaesthetized rats after slow intravenous administration (during 5 minutes) of 3-(1H-imidazol-4-ylmethyl)-indan-5-ol at the doses of 1 and 3 µg/kg. Means±SEM of percent changes from the baseline value are shown, n=6 in each group.
Figure 2:
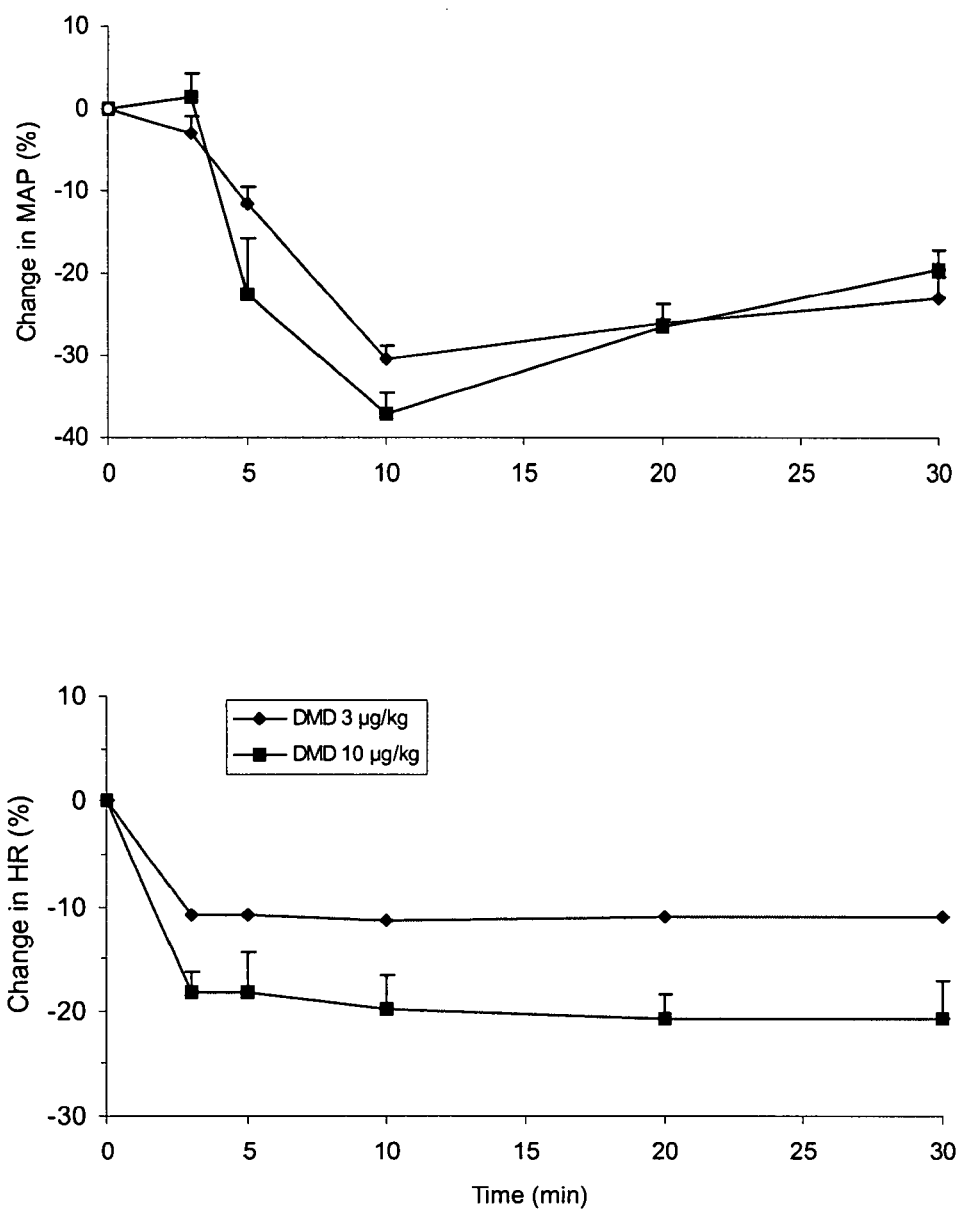
FIG. 2 shows the time-course of mean arterial pressure (MAP) (upper) and heart rate (HR) (lower) in anaesthetized rats after slow intravenous administration (during 5 minutes) of dexmedetomidine (DMD) at the doses of 3 and 10 µg/kg. Means±SEM of percent changes from baseline value are shown, n=6 in each group.

+31%) and long-lasting decrease in HR (maximally −19%) after slow (during 5 minutes) i.v. dosing of 1 and 3 µg/kg (see FIG. 1 and Table 1). Instead, the reference compound dexmedetomidine (3 and 10 µg/kg) decreased both MAP and HR (maximally −37% and −21%, respectively) immediately and dose-dependently (see FIG. 2 and Table 1) after slow intravenous administration at the tested doses.

TABLE 1

The effects of 3-(1H-imidazol-4-ylmethyl)-indan-5-ol and dexmedetomidine on mean arterial pressure (MAP) and heart rate (HR) after slow (during 5 minutes) intravenous administration in anaesthetized rats.

| Dose (µg/kg) | Time (min) | MPV-2426 Al MAP (mmHg) | HR (beats/min) | Dose (µg/kg) | Time (min) | Dexmedetomidine MAP (mmHg) | HR (beats/min) |
|---|---|---|---|---|---|---|---|
| 1 | 0 | 97 ± 4 | 373 ± 8 | 3 | 0 | 89 ± 5 | 348 ± 12 |
|   | 3 | 114 ± 3 | 324 ± 9 |   | 3 | 86 ± 5 | 310 ± 6 |
|   | 5 | 112 ± 3 | 321 ± 9 |   | 5 | 79 ± 7 | 310 ± 5 |
|   | 10 | 83 ± 4 | 327 ± 7 |   | 10 | 61 ± 4 | 308 ± 4 |
|   | 20 | 84 ± 4 | 319 ± 9 |   | 20 | 65 ± 2 | 309 ± 5 |
|   | 30 | 80 ± 3 | 317 ± 9 |   | 30 | 67 ± 2 | 309 ± 5 |
| 3 | 0 | 94 ± 5 | 366 ± 11 | 10 | 0 | 92 ± 2 | 383 ± 11 |
|   | 3 | 123 ± 9 | 309 ± 7 |   | 2 | 94 ± 4 | 308 ± 5 |
|   | 5 | 117 ± 12 | 311 ± 4 |   | 5 | 75 ± 6 | 309 ± 3 |
|   | 10 | 88 ± 4 | 321 ± 4 |   | 10 | 59 ± 3 | 303 ± 3 |
|   | 20 | 83 ± 5 | 321 ± 6 |   | 20 | 68 ± 2 | 296 ± 7 |
|   | 30 | 77 ± 3 | 305 ± 6 |   | 30 | 73 ± 2 | 297 ± 6 |

The values are means ± SEM, n = 6 in each group.

The invention will be further clarified by the following example, which is intended to be purely exemplary of the invention.

EXAMPLE 1

The effects of 3-(1H-imidazol-4-ylmethyl)-indan-5-ol on blood pressure and heart rate after slow intravenous administration were studied in anaesthetized rats. Dexmedetomidine (Orion Corporation Orion Pharma, Finland), a specific $\alpha_2$-adrenoceptor agonist was studied as a reference compound.

Male Sprague-Dawley rats (B&K, Sweden), weighing 290-400 g, were anaesthetized with sodium pentobarbital (Mebunat® 60 mg/ml) 75 mg/kg i.p. The left femoral vein was cannulated (PE-50) for slow drug injections. The left femoral artery was cannulated (PE-60) and the mean arterial blood pressure (MAP) and heart rate (HR) were recorded continuously via a Micro MP-15 transducer connected to a Grass Model 7D Polygraph. Arterial pressure was sampled at a rate 150 samples/second and recorded on a Pinus PC computer using the software program AcqKnowledge version 3.5.3 and a MP100A data acquisition unit for analog/digital conversion (BIOPAC Systems, Inc.). Pulse waves of the blood pressure were used for displaying heart rate continuously. The body temperature (rectal) was kept constant at 37±0.5° C. by warming with a lamp above the animal's chest. Only rats with MAP of 73 mmHg or higher were used for the tests. After a stabilizing period of 10-20 min, 3-(1H-imidazol-4-ylmethyl)-indan-5-ol (1 and 3 µg/kg, as hydrochloride) or dexmedetomidine (3 and 10 µg/kg, as hydrochlorides) dose was given as slow intravenous injection (during 5 min) by an infusion pump (Perfusor® ED 2, B. Braun). The total injection volume was adjusted to 1 ml in each experimental group.

3-(1H-imidazol-4-ylmethyl)-indan-5-ol induced an immediate and dose-dependent increase in MAP (maximally Immediate and dose-dependent initial hypertensive action was seen after administration of 3-(1H-imidazol-4-ylmethyl)-indan-5-ol at all tested doses. In addition, immediate, and long-lasting bradycardic action was noted after administration 3-(1H-imidazol-4-ylmethyl)-indan-5-ol at all tested doses. Instead, the reference compound dexmedetomidine (3 and 10 µg/kg) decreased both MAP and HR after slow intravenous administration. After slow intravenous administration 3-(1H-imidazol-4-ylmethyl)-indan-5-ol produces both hypertensive and bradycardic actions, unlike dexmedetomidine, which in turn has typical cardiovascular effects of an alpha-2-adrenoceptor agonist.

Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The references discussed herein are specifically incorporated by reference in their entirety.

The invention claimed is:

1. A method for the treatment of hypotension and shock due to low peripheral resistance, comprising administering to a mammal in need thereof an effective amount of an imidazole derivative of formula I:

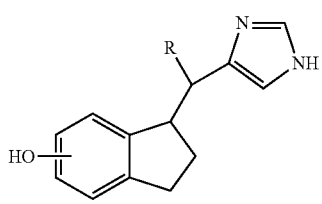

wherein R is hydrogen or methyl, or a pharmaceutically acceptable ester or salt thereof.

2. The method according to claim 1, wherein 3-(1H-imidazol-4-ylmethyl)-indan-5-ol is administered.

3. The method according to claim 2, wherein 3-(1H-imidazol-4-ylmethyl)-indan-5-ol hydrochloride is administered.

4. The method according to claim 1, wherein the administration is intravenous.

5. The method according to claim 1, wherein the mammal is a human.

6. The method according to claim 4, wherein the effective amount administered is about 10-500 μg/patient.

7. The method according to claim 6, wherein the effective amount administered is about 30-200 μg/patient.

8. The method according to claim 2, wherein the administration is intravenous.

9. The method according to claim 3, wherein the administration is intravenous.

10. The method according to claim 2, wherein the mammal is a human.

11. The method according to claim 3, wherein the mammal is a human.

12. The method according to claim 4, wherein the mammal is a human.

13. The method according to claim 5, wherein the effective amount administered is about 10-500 μg/patient.

* * * * *